(12) United States Patent
Imamura

(10) Patent No.: US 10,674,902 B2
(45) Date of Patent: Jun. 9, 2020

(54) INFORMATION PROCESSING APPARATUS, OPERATION METHOD THEREOF, AND COMPUTER PROGRAM

(71) Applicant: CANON KABUSHIKI KAISHA, Tokyo (JP)

(72) Inventor: Hiroshi Imamura, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 189 days.

(21) Appl. No.: 15/138,676

(22) Filed: Apr. 26, 2016

(65) Prior Publication Data

US 2016/0317014 A1 Nov. 3, 2016

(30) Foreign Application Priority Data

Apr. 30, 2015 (JP) ................. 2015-093541

(51) Int. Cl.
| | | |
|---|---|---|
| *A61B 3/14* | (2006.01) | |
| *A61B 3/10* | (2006.01) | |
| *A61B 3/00* | (2006.01) | |
| *A61B 3/113* | (2006.01) | |
| *A61B 3/12* | (2006.01) | |

(52) U.S. Cl.
CPC .......... *A61B 3/0025* (2013.01); *A61B 3/0041* (2013.01); *A61B 3/1025* (2013.01); *A61B 3/113* (2013.01); *A61B 3/1233* (2013.01); *A61B 3/14* (2013.01)

(58) Field of Classification Search
CPC ....... A61B 3/1025; A61B 3/0025; A61B 3/14; A61B 3/1233; A61B 3/113; A61B 3/1225; A61B 3/0041; A61B 3/0058; A61B 3/102; A61B 3/152; A61B 2017/00694; A61B 2560/0475; A61B 3/0008; A61B 3/1015; A61B 3/12; A61B 3/1241; A61B 5/024; A61B 5/025
USPC ........ 351/200, 205, 206, 209–211, 221, 222, 351/223, 243–246, 247
See application file for complete search history.

(56) References Cited

U.S. PATENT DOCUMENTS

| | | | |
|---|---|---|---|
| 6,341,035 B1 | 1/2002 | Miura et al. | |
| 6,687,052 B1 * | 2/2004 | Wilson | ............... G02B 21/0024 359/234 |
| 2005/0225725 A1 | 10/2005 | Warden et al. | |
| 2012/0062842 A1 * | 3/2012 | Griggio | ................ A61B 3/0091 351/209 |

(Continued)

OTHER PUBLICATIONS

Sulai, Y., et al., "Visualization of retinal vascular structure and perfusion with a nonconfocal adaptive optics scanning light ophthalmoscope", J. Opt. Soc. Am. A, Mar. 2014, pp. 569-579, vol. 31, No. 3.

(Continued)

*Primary Examiner* — Brandi N Thomas
(74) *Attorney, Agent, or Firm* — Canon U.S.A., Inc,. IP Division

(57) ABSTRACT

An information processing apparatus includes: an image acquiring unit configured to acquire a plurality of types of images including a plurality of confocal images obtained by imaging an eye at different times, and a plurality of non-confocal images temporally corresponding to the plurality of confocal images; and an information acquiring unit configured to acquire information indicating a positional gap of at least one of the plurality of types of images, based on the plurality of non-confocal images.

30 Claims, 10 Drawing Sheets

(56) References Cited

U.S. PATENT DOCUMENTS

2013/0293841 A1    11/2013  Frison et al.
2014/0340426 A1*  11/2014  Furuhata ................. G06T 11/60
                                                                  345/635

OTHER PUBLICATIONS

Scoles, D., et al., "In Vivo Imaging of Human Cone Photoreceptor Inner Segments", IOVS, Jul. 2014, pp. 4244-4251, vol. 55, No. 7.

* cited by examiner

INFORMATION PROCESSING APPARATUS, OPERATION METHOD THEREOF, AND COMPUTER PROGRAM

BACKGROUND OF THE INVENTION

Field of the Invention

The present invention relates to an information processing apparatus used in ophthalmological diagnosis and treatment, an operation method thereof, and a computer program.

Description of the Related Art

Examination of the eye is widely performed for early diagnosis and treatment of lifestyle diseases and diseases which are primary causes of loss of eyesight. The scanning laser ophthalmoscope (SLO), which is an ophthalmological apparatus that employs the principle of confocal laser scanning microscopy, performs high speed raster scanning of a subject's eye with a laser beam, which is measurement light, and acquires a high-resolution planar image of the fundus from the intensity of returning light. In confocal laser scanning microscopy, detecting only light that has passed through an aperture (pinhole) enables an image to be formed just using returning light of a particular depth position (focal point), and therefore images with higher contrast than those obtained by fundus cameras and the like can be acquired. An apparatus that obtains such high-contrast planar images will hereinafter be referred to as an SLO apparatus, and a planar image obtained thusly is referred to as an SLO image.

In recent years, increased beam diameter of measurement light in SLO apparatuses has enabled acquisition of SLO images of the retina, with improved horizontal resolution. However, the increased beam diameter of the measurement light has led to a problem of deterioration the S/N ratio and the resolution of the SLO image during acquisition of SLO images of the retina, due to aberration of the eye being examined. An adaptive optic SLO apparatus has been developed to solve this problem. The adaptive optic SLO apparatus has an adaptive optic system that measures aberration of the eye being examined in real time using a wavefront sensor, and corrects aberration occurring in the eye being examined with regard to the measurement light and the returning light thereof using a wavefront correction device. This enables the acquisition of SLO images with high resolution in the horizontal or main-scanning direction so that a high-magnification image can be acquired.

Such a high resolution SLO image can be acquired as a moving image. In order to noninvasively observe hemodynamics (dynamics of blood flow), for example, retinal blood vessels are extracted from each frame, and the moving speed of blood cells through capillaries and so forth is measured. Also, in order to evaluate the relation with visual function using an SLO image, photoreceptors P are detected, and the density distribution and array of the photoreceptors P are calculated. FIG. 6B illustrates an example of a high horizontal resolution SLO image. The photoreceptors P, a low-luminance region Q corresponding to the position of capillaries, and a high-luminance region W corresponding to the position of a white blood cell, can be observed. In a case of observing photoreceptors P in the SLO image, the focus position is set nearby the outer layer of the retina (B5 in FIG. 6A) to take a SLO image such as in FIG. 6B. On the other hand, there are retinal blood vessels and capillaries that have branched running through the inner layers of the retina (B2 through B4 in FIG. 6A). Acquiring an adaptive optics SLO image with the focus position set in the inner layers of the retina enables the retinal blood vessel walls to be directly observed.

However, confocal images taken of the inner layers of the retina have intense noise signals due to the influence of light reflecting from the nerve fiber layer, and there have been cases where observing blood vessel walls and detection of wall boundaries has been difficult. Accordingly, as of recent, techniques have come into use using observation of non-confocal images obtained by acquiring scattered light, by changing the diameter, shape, and position of a pinhole on the near side of the light receiving portion. This is described in Sulai, Dubra et al.; "Visualization of retinal vascular structure and perfusion with a nonconfocal adaptive optics scanning light ophthalmoscope", J. Opt. Soc. Am. A, Vol. 31, No. 3, pp. 569-579, 2014 (hereinafter "Sulai and Dubra"). Non-confocal images have a great depth of focus, so objects that have unevenness in the depth direction, such as blood vessels can be easily observed, and also noise is reduced since reflected light from the nerve fiber layer is not readily directly received. While observation of photoreceptors at the outer layers of the retina has primarily involved imaging confocal images of the outer segment of photoreceptors, it has been found that the unevenness of the inner segment of photoreceptors can be imaged in non-confocal images. This is described in Scoles, Dubra et al.; "In vivo Imaging of Human Cone Photoreceptor Inner Segment", IOVS, Vol. 55, No. 7, pp. 4244-4251, 2014 (hereinafter "Scoles and Dubra". In early stages of a photoreceptor disorder, a region where an initial disorder has damaged the outer segment but the inner segment has survived is imaged as a black defect area in confocal images (Dc5 in FIG. 6K), but can be observed as a region where high-luminance granular objects exist in non-confocal images (Dn5 in FIG. 6L). Sulai and Dubra disclose technology for acquiring non-confocal images of retinal blood vessels using an adaptive optics SLO apparatus, while Scoles and Dubra disclose technology for acquiring both confocal images and non-confocal images at the same time using an adaptive optics SLO apparatus.

SUMMARY OF THE INVENTION

An information processing apparatus and operation method thereof according to the present invention include: an image acquiring unit configured to acquire a plurality of types of images including a plurality of confocal images obtained by imaging an eye at different times, and a plurality of non-confocal images temporally corresponding to the plurality of confocal images; and an information acquiring unit configured to acquire information indicating a positional gap of at least one of the plurality of types of images, based on the plurality of non-confocal images.

An operation method of an information processing apparatus includes: a step of acquiring a plurality of types of images including a plurality of confocal images obtained by imaging an eye at different times, and a plurality of non-confocal images temporally corresponding to the plurality of confocal images; and a step of acquiring information indicating a positional gap of at least one of the plurality of types of images, based on the plurality of non-confocal images.

Further features of the present invention will become apparent from the following description of exemplary embodiments with reference to the attached drawings.

DESCRIPTION OF THE EMBODIMENTS

In SLO apparatuses capable of taking confocal images and non-confocal images, image positioning is generally performed using confocal signals, since the confocal signals have stronger signal intensity. However, in a case of setting the focus position at the inner layer of the retina and photographing retinal blood vessels by adaptive optics SLO for example, performing positioning using confocal signals results in the peak positions in the evaluation value distribution for positioning similarity readily varying due to the influence of noise, and there has been a problem that positioning is imprecise. Even when setting the focus position at the outer layer of the retina and photographing photoreceptors, the similarity evaluation values are low among images at photoreceptor defect portions, since there are few high-luminance regions to serve as guides for positioning, and there has been a problem that positioning is imprecise.

It has been found desirable to improve accuracy in finding a positional gap in confocal images.

Figure 1:
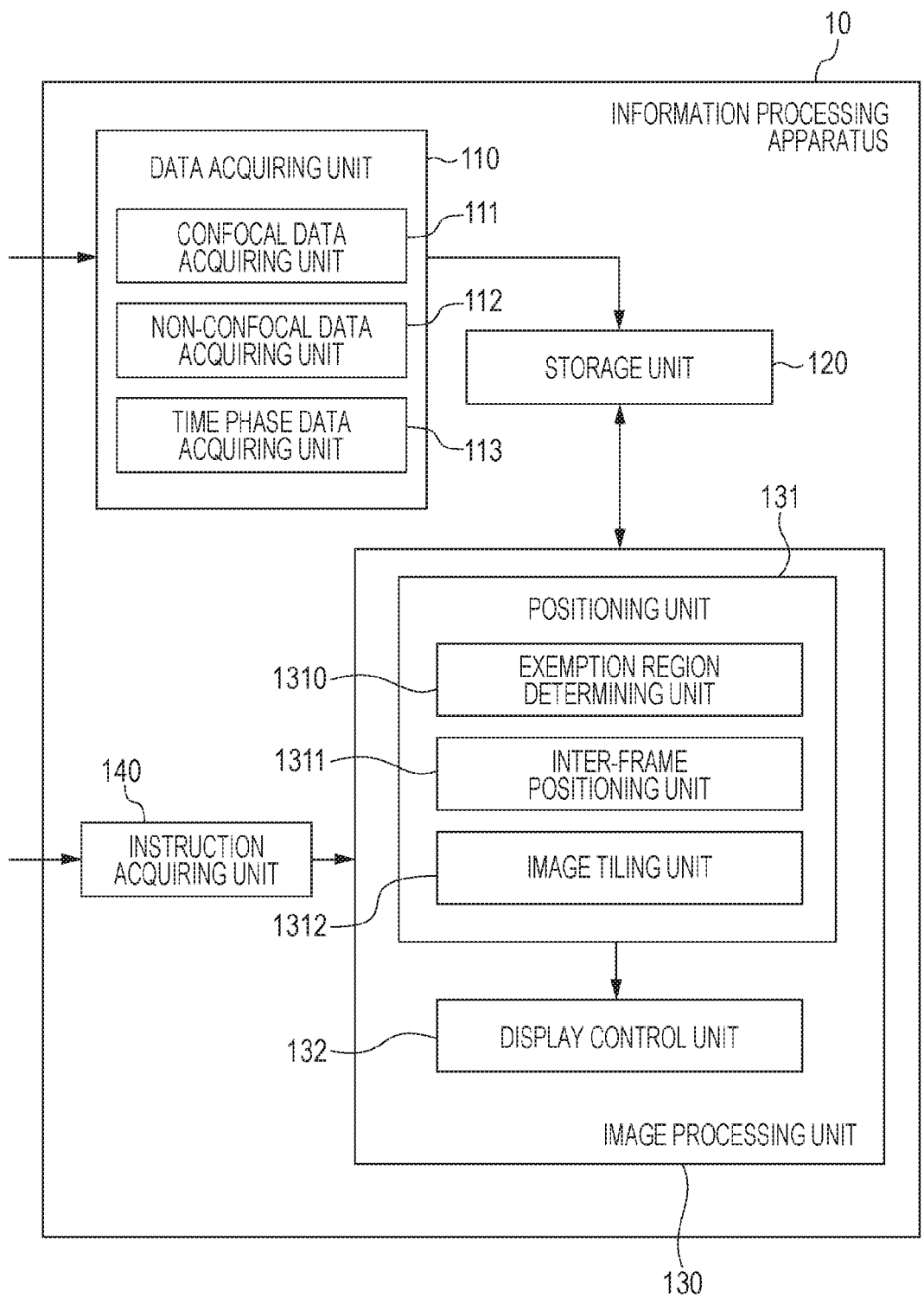
FIG. 1 is a block diagram illustrating a functional configuration example of an information processing apparatus according to a first embodiment.

Accordingly, one aspect of an embodiment includes an image acquiring unit configured to acquire multiple types of images including multiple types of confocal images and at least one type of non-confocal image by imaging an eye at different times, (e.g., a data acquiring unit 110 in FIG. 1). Also, one aspect of an embodiment includes an information acquiring unit configured to acquire information indicating a positional gap of at least one of the multiple types of images, based on a plurality of non-confocal images of at least one type (e.g., an image processing unit 130 in FIG. 1). Accordingly, accuracy of obtaining positional gaps of confocal images can be improved. Now, information indicating a positional gap is an evaluation value of image similarity or the like, and is also referred to as a positioning parameter or the like in the present specification.

Also, one aspect of an embodiment may further include a positioning unit configured to position at least one of multiple types of images based on information indicating a positional gap, for example (e.g., a positioning unit 131 in FIG. 1). Accordingly, information indicating positional gaps of confocal images with high accuracy can be used, so consequently, the accuracy of positioning of confocal images can be improved. Note that an ophthalmologic imaging apparatus (e.g., an SLO imaging apparatus 20) may be controlled to track an eye before acquiring an image or while acquiring an image, besides positioning images after image acquisition. Preferably included here is a control unit configured to control a scanning optical system that scans light by which the eye is irradiated, based on information indicating a positional gap. Also preferably included is control unit configured to control a driving unit that drives an optical head (a casing covering the scanning optical system) of the ophthalmologic imaging apparatus as to a stage. An example of the control unit is the data acquiring unit 110 in FIG. 1. The control unit does not have to be provided to the information processing apparatus 10, and may be made up of a central processing unit (CPU) or the like provided to the ophthalmologic imaging apparatus.

Also, one aspect of another embodiment is an apparatus that acquires confocal images and non-confocal images, that preferably decides positioning parameter values based on non-confocal images. Accordingly, Not only non-confocal images but also confocal images can be positioned using the parameter values. Accordingly, robust and highly accurate image processing can be performed even regarding images taken of blood vessels at the inner layer of the retina and disorders on the outer layer of the retinal.

Now, the technology discussed in Sulai and Dubra preforms image positioning using non-confocal images in an adaptive optics SLO apparatus that acquires non-confocal images. A method for deciding positioning parameter values using non-confocal images when acquiring confocal images and non-confocal images, and performing positioning applying the positioning parameter values, decided for the non-confocal images, to the confocal images as well, is not disclosed therein. The technology discussed in Scoles and Dubra acquires confocal images and non-confocal images at the same time, but performs positioning using confocal images. Performing accurate positioning is difficult with images where confocal signal values are low in locations such as photoreceptor defect regions and the similarity evaluation value tends to be low.

Preferred embodiments of an information processing apparatus, the operation method thereof, and a computer program, according to the present invention, will be described below in detail with reference to the drawings. It should be noted that the present invention is not restricted to these.

Figure 3A:
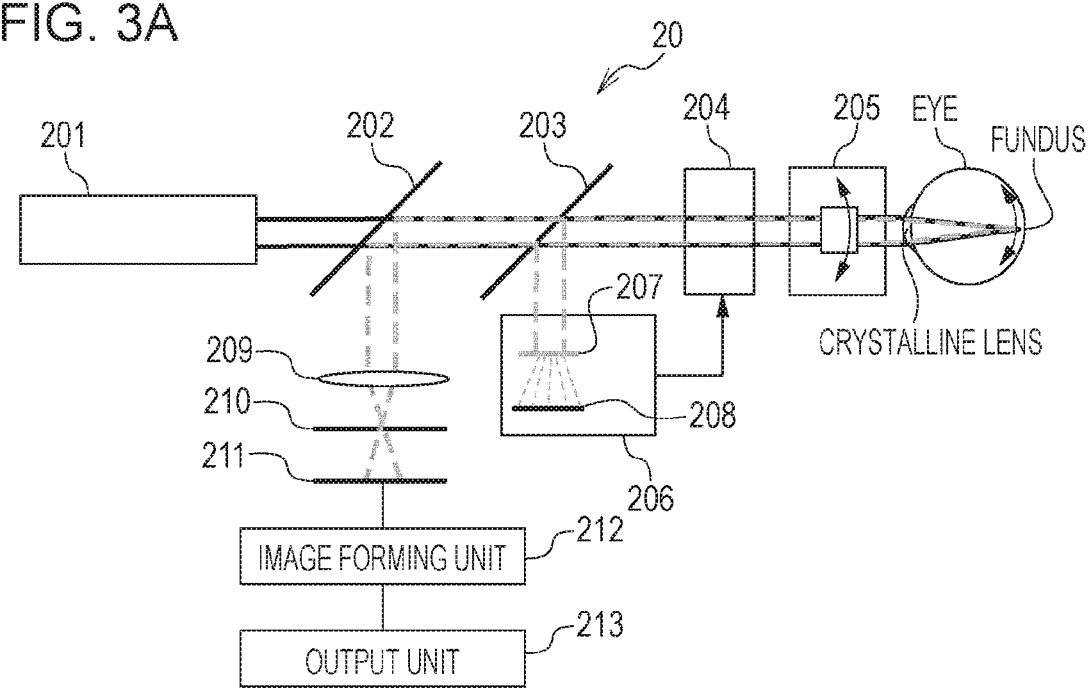
FIGS. 3A through 3D are diagrams for describing the overall configuration of an SLO imaging apparatus according to the first embodiment.
Figure 3B:
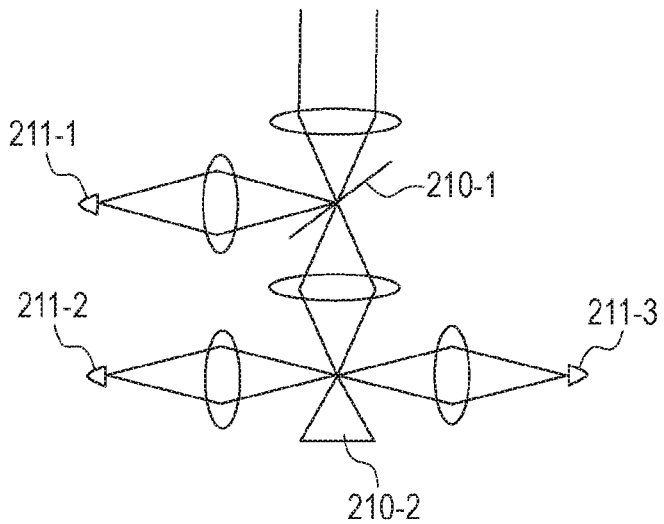

First Embodiment: Acquiring Positioning Parameters Using Non-Confocal Images The information processing apparatus according to a first embodiment is configured to position confocal images and non-confocal images using positioning parameters decided based on non-confocal images, when imaging retinal blood vessels using an SLO apparatus that acquires confocal images and non-confocal images at generally the same time. Specifically, confocal images Dc and non-confocal images Dn relating to retinal blood vessels are acquired using an SLO apparatus such as illustrated in FIGS. 3A and 3B, that acquires confocal images Dc and non-confocal images Dn at generally the same time. Description will be made regarding a case of using positioning parameter values decided based on the non-confocal images Dn to perform inter-frame positioning and image tiling processing of confocal images Dc and non-confocal images Dn. Note that the confocal images and non-confocal images do not have to be taken at exactly the same time, it is sufficient if they temporally correspond. For example, it is sufficient if the confocal images and non-confocal images are acquired time interval where positional gaps of images due to eye movement is relatively small.

Overall Configuration

Figure 2:
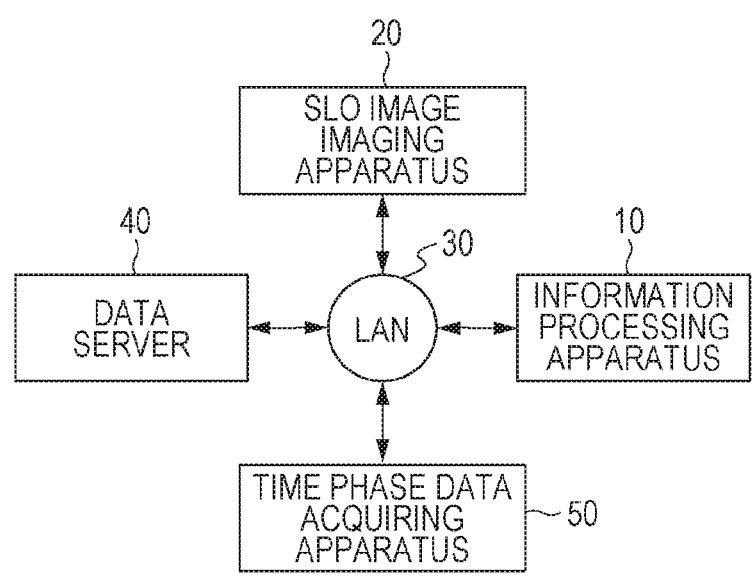
FIG. 2 is a block diagram illustrating configuration examples of a system including the information processing apparatus according to the first embodiment.

FIGS. 2A and 2B are configuration diagrams of a system including the information processing apparatus 10 according to the present embodiment. The information processing apparatus 10 is communicably connected to an SLO imaging apparatus 20, which is an example of an ophthalmic imaging apparatus, a data server 40, and a time phase data acquisition apparatus 50, via a local area network (LAN) 30 including optical fiber, Universal Serial Bus (USB), IEEE 1394, or the like, as illustrated in FIGS. 2A and 2B. The configuration of communicable connection to these devices may be via an external network such as the Internet, or may be a configuration where the information processing apparatus 10 is directly connected to the SLO imaging apparatus 20. Alternatively, the information processing apparatus 10 may be integrally built into an ophthalmic imaging apparatus.

The SLO imaging apparatus 20 is an apparatus to obtain confocal images Dc and non-confocal images Dn, which are wide-angle images Dl and high-magnification images Dh of the eye. The SLO imaging apparatus 20 transmits wide-angle images Dl, confocal images Dc, non-confocal images Dn, and information of fixation target positions F1 and Fcn used for imaging thereof, to the information processing apparatus 10 and the data server 40. The time phase data acquisition apparatus 50 is an apparatus that acquires biosignal data (time phase data) that autonomously and cyclically changes, such as a sphygmograph or electrocardiograph, for example. The time phase data acquisition apparatus 50 acquires time phase data Pi at the same time as acquiring the wide-angle images Dl, confocal images Dc, and non-confocal images Dn, in accordance with operations performed by an unshown operator. The acquired time phase data Pi is sent to the information processing apparatus 10 and data server 40. The time phase data acquisition apparatus 50 may be directly connected to the SLO imaging apparatus 20. In a case where these images are acquired at different imaging positions, this is expressed as Dli, Dcj, Dnk. That is to say, i and j are variables indicating the numbers for the imaging positions, where i=1, 2, . . . , imax, j=1, 2, . . . , jmax and k=1, 2, . . . , kmax. In a case of acquiring confocal images Dc and non-confocal images Dn at different magnifications, this is expressed like Dc1$m$, Dc2$o$, . . . (Dn1$m$, Dn2$o$, . . . ) in order from the highest-magnification image, with Dc1$m$ (Dn1$m$) denoting high-magnification confocal (non-confocal) images, and Dc2$o$, . . . (Dn2$o$, . . . ) denoting mid-magnification images.

The data server 40 holds the wide-angle images Dl, confocal images Dc, and non-confocal images Dn, of the examinee eye, imaging conditions data such as fixation target positions F1 and Fcn used for the imaging thereof, time phase data Pi, image features of the eye, and so forth. In the present invention, image features relating to the photoreceptors P, capillaries Q, blood cells W, and retinal blood vessel walls, are handled as image features of the eye. The wide-angle images Dl, confocal images Dc, and non-confocal images Dn output from the SLO imaging apparatus 20, fixation target positions F1 and Fcn used for the imaging thereof, time phase data Pi output from the time phase data acquisition apparatus 50, and image features of the eye output from the information processing apparatus 10, are saved in the server 40. Also, the wide-angle images Dl, confocal images Dc, and non-confocal images Dn, time phase data Pi, and image features of the eye, are transmitted to the information processing apparatus 10 in response to requests from the information processing apparatus 10.

Next, the functional configuration of the information processing apparatus 10 according to the present embodiment will be described with reference to FIG. 1. FIG. 1 is a block diagram illustrating the functional configuration of the information processing apparatus 10. The information processing apparatus 10 includes a data acquiring unit 110, a storage unit 120, an image processing unit 130, and an instruction acquiring unit 140. The data acquiring unit 110 includes a confocal data acquiring unit 111, a non-confocal data acquiring unit 112, and a time phase acquiring unit 113. The image processing unit 130 includes a positioning unit 131 and a display control unit 132. The positioning unit 131 further has an exemption region determining unit 1310, inter-frame positioning unit 1311, and image tiling unit 1312.

Now, the SLO imaging apparatus 20 that applies adaptive optics will be described with reference to FIGS. 3A and 3B. The SLO imaging apparatus 20 includes a superluminescent diode (SLD) 201, a Shack-Hartman wavefront sensor 206, an adaptive optics system 204, beam splitters 202 and 203, an X-Y scanning mirror 205, a focus lens 209, a diaphragm 210, a photosensor 211, an image forming unit 212, and an output unit 213.

Light irradiated from the SLD 201 that is the light source is reflected at the fundus. Part of the reflected light is input to the Shack-Hartman wavefront sensor 206 via the second beam splitter 203, and the remaining reflected light is input to the photosensor 211 via the first beam splitter 202. Although the light source here services both as a light source for acquiring confocal images and a light source for acquiring non-confocal images, multiple light sources configured to emit different wavelengths may be used, or the like. The Shack-Hartman wavefront sensor 206 is a device to measure aberration of the eye, in which a lens array 207 is connected to a charge-coupled device (CCD) 208. Upon input light being transmitted through the lens array 207, a bright point set appears on the CCD 208, and wave aberration is measured base on the positional gap of the projected bright points. The adaptive optics system 204 drives an aberration correction device (deformable mirror or spatial light phase modulator) to correct the aberration, based on the wave aberration measured by the Shack-Hartman wavefront sensor 206. The light subjected to aberration-correction passes through the focus lens 209 and diaphragm 210, and is received at the photosensor 211. The diaphragm 210 and photosensor 211 are examples of an aperture and an optical sensor according to the present invention. The aperture preferably is provided upstream of and near to the optical sensor. The scanning position on the fundus can be controlled by moving the X-Y scanning mirror 205, thereby acquiring data according to an imaging region and time (frame rate×frame count) that the operator has instructed. The data is transmitted to the image forming unit 212, where image distortion due to variation in scanning rate is corrected and luminance value correction is performed, thereby forming image data (moving image or still image). The output unit 213 outputs the image data formed by the image forming unit 212.

The configuration of the diaphragm 210 and photosensor 211 portion in FIG. 3A is optional, just as long as the SLO imaging apparatus 20 is configured to be able to acquire confocal images Dc and non-confocal images Dn. The present embodiment is configured using a light-shielding member 210-1 (FIGS. 3B and 3C) and photosensor 211-1, 211-2, and 211-3 (FIG. 3B). Regarding the returning light in FIG. 3B, part of the light that has entered the light-shielding member 210-1 disposed at the image forming plate is reflected and enters the photosensor 211-1. Now, the light-shielding member 210-1 will be described with reference to FIG. 3C. The light-shielding member 210-1 is formed of transmitting regions 210-1-2 and 210-1-3, a light-shielded region (omitted from illustration), and a reflecting region 210-1-1, so that the center is positioned on the center of the optical axis of the returning light. The light-shielding member 210-1 has an elliptic shape pattern so that when disposed obliquely as to the optical axis of the returning light, the shape appears to be circular when seen from the optical axis direction. The returning light divided at the light-shielding member 210-1 is input to the photosensor 211-1. The returning light that has passed through the transmitting regions 210-1-2 and 210-1-3 of the light-shielding member 210-1 is split by a quadrangular pyramid prism 210-2 disposed at the image forming plane, and is input to photosensors 211-2 and 211-3, as illustrated in FIG. 3B. Voltage signals obtained at the photosensors are converted into digital values at an AD board within the image forming unit 212, thereby forming a two-dimensional image. The image based on light entering the photosensor 211-1 is a confocal image where focus has been made on a particular narrow range. Images based on light entering the photosensors 211-2 and 211-3 are non-confocal images where focus has been made on a broad range. The light-shielding member 210-1 is an example of an optical member that divides returning light from the eye which has been irradiated by light from the light source, into returning light passing through a confocal region and returning light passing through a non-confocal region. The transmitting regions 210-1-2 and 210-1-3 are examples of a non-confocal region, and non-confocal images are acquired based on the returning light passing through the non-confocal regions. The reflecting region 210-1-1 is an example of a confocal region, and confocal images are acquired based on the returning light passing through the confocal region.

Figure 3C:
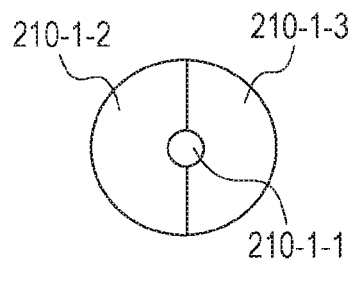
Figure 3D:
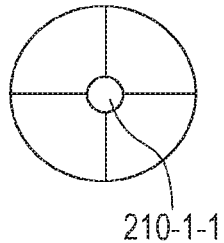

The method for dividing non-confocal signals is not restricted to this, and a configuration may be made where non-confocal signals are divided into four and received, such as illustrated in FIG. 3D, for example. Also, the reception method of confocal signals and non-confocal signals is not restricted to this. For example, a mechanism is preferably had where the diameter and position of the diaphragm 210 (aperture) is changeable. In doing so, at least one of the diameter of the aperture and the position in the optical axis direction is configured so as to be adjustable, so as to receive as confocal signals as illustrated in FIG. 3C and to receive as non-confocal signals as illustrated in FIG. 3D. The diameter and movement amount of the aperture may be optionally adjusted. For example, FIG. 3C shows that the diameter of the aperture can be adjusted to around 1 Airy disc diameter (ADD), and FIG. 3D shows that the diameter of the aperture can be adjusted to around 10 ADD with a movement amount of around 6 ADD. Alternatively, a configuration may be made where multiple non-confocal signals are received at the same time. There are two types of non-confocal signals in the present embodiment, so one will be denoted by Dnr referring to the R channel image, and the other will be denoted by Dnl referring to the L channel image. The notation "non-confocal image Dn" refers to both the R channel image Dnr and L channel image Dnl.

The SLO imaging apparatus 20 can also operate as a normal SLO apparatus, by increasing the scan angle of the scanning optical system in the configuration in FIG. 3A, and instructing so that the adaptive optics system 204 does not perform aberration correction, so as to image wide-angle confocal images and non-confocal images. Images which are lower magnification than the high-magnification images Dc and Dn, and have the lowest magnification of images acquired by the data acquiring unit 110 will hereinafter be referred to as wide-angle images Dl (Dlc, Dlr, Dll). Accordingly, a wide-angle image Dl may be an SLO image where adaptive optics has been applied, and cases where a simple SLO image are also included. Note that when distinguishing between confocal wide-angle images and non-confocal wide-angle images Dl, these are denoted by Dlc, Dlnr, and Dlnl.

Figure 4:
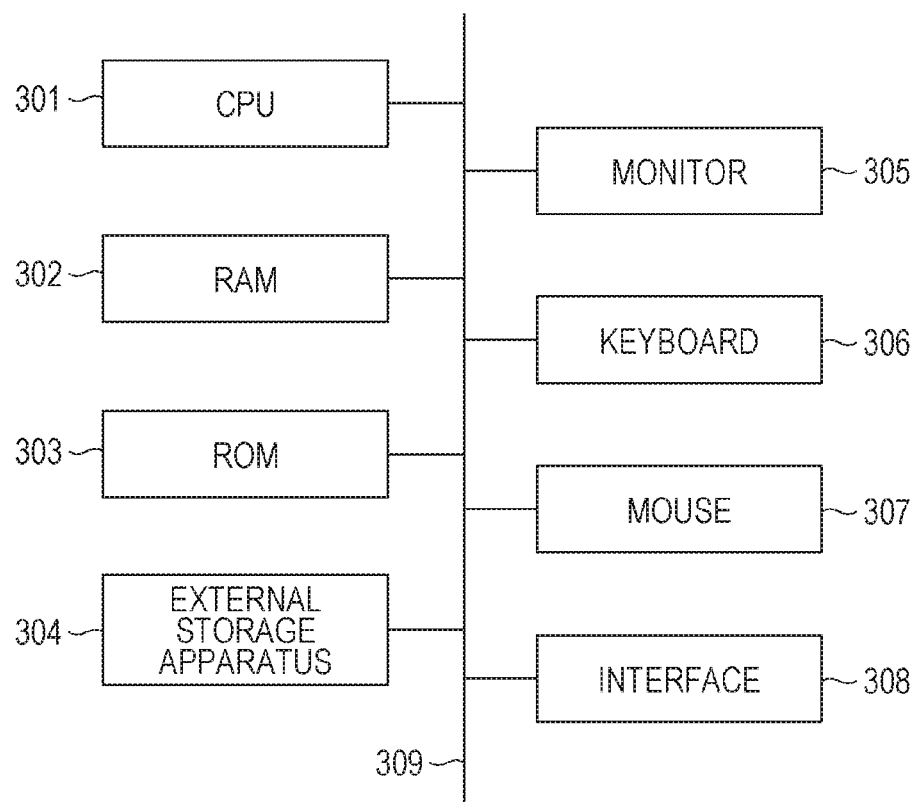
FIG. 4 is a block diagram illustrating a hardware configuration example of a computer which has hardware equivalent to a storage unit and image processing unit and holds other units as software which is executed.
Figure 5A:
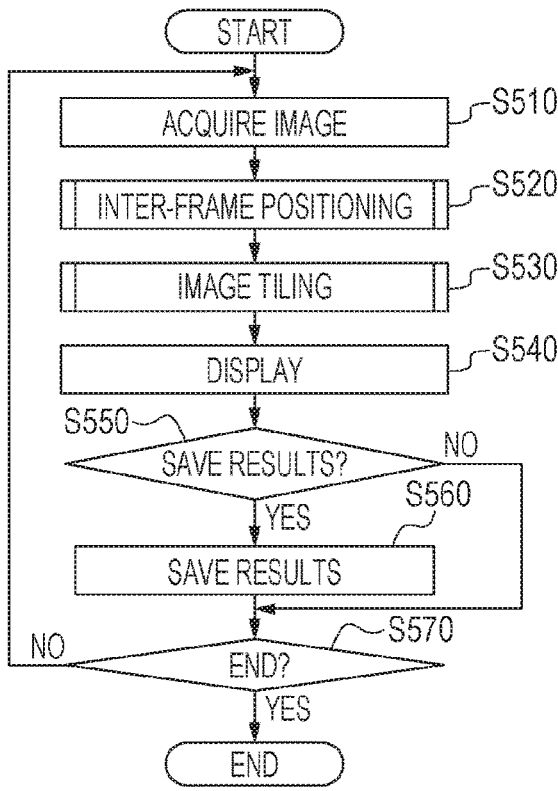
FIGS. 5A through 5C are flowcharts of processing which the information processing apparatus according to the first embodiment executes.

Next, the hardware configuration of the information processing apparatus 10 will be described with reference to FIG. 4. In FIG. 4, 301 denotes a central processing unit (CPU), 302 memory (random access memory (RAM)), 303 control memory (read-only memory (ROM)), 304 an external storage device, 305 a monitor, 306 a keyboard, 307 a mouse, and 308 an interface. Control programs for realizing the image processing functions according to the present embodiment, and data used at the time of the control programs being executed, are stored in the external storage device 304. The control programs and data are loaded to the RAM 302 via a bus 309 as appropriate under control of the CPU 301, executed by the CPU 301, and function as the units described below. The functions of the blocks making up the information processing apparatus 10 will be correlated with specific execution procedures of the information processing apparatus 10 illustrated in the flowchart in FIG. 5A.

Step S510: Acquiring Images

Figure 6A:
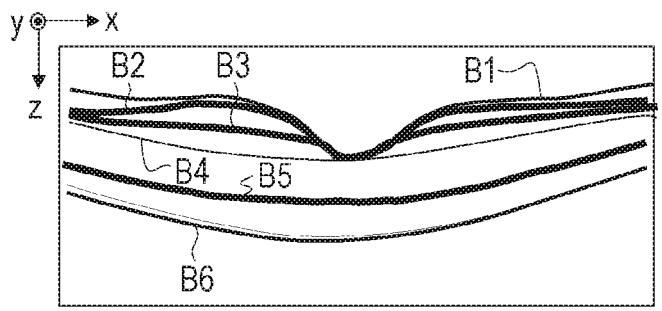
FIGS. 6A through 6L are diagrams illustrating what is performed in image processing according to the first embodiment.
Figure 6B:
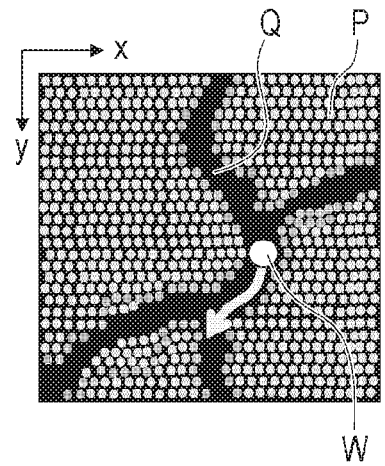
Figure 6C:
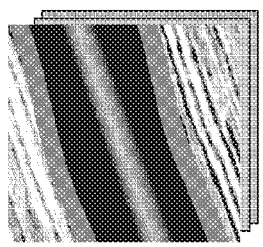
Figure 6D:
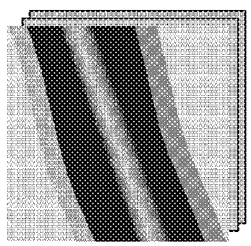

The data acquiring unit 110 requests the SLO imaging apparatus 20 for wide-angle images Dlc, Dlr, and Dll, confocal images Dcj, non-confocal images Dnrk and Dnlk, and corresponding fixation target positions Fl and Fcn. The SLO imaging apparatus 20 acquires and transmits the wide-angle images Dlc, Dlr, and Dll, confocal images Dcj, non-confocal images Dnrk and Dnlk, and corresponding fixation target positions Fl and Fcn in responds to the acquisition request. The data acquiring unit 110 receives the SLO imaging apparatus 20 for wide-angle images Dlc, Dlr, and Dll, confocal images Dcj, non-confocal images Dnrk and Dnlk, and corresponding fixation target positions Fl and Fcn, from the SLO imaging apparatus 20 via the LAN 30, and stores these in the storage unit 120. The time phase data acquiring unit 113 requests the time phase data acquisition apparatus 50 for time phase data Pi relating to biological signals. In the present embodiment, a sphygmograph serves as a time phase data acquisition apparatus, used to acquire pulse wave data Pi from the earlobe of the subject. This pulse wave data Pi is expressed with acquisition time on one axis and a cyclic point sequence having the pulse wave signal values measured by the sphygmograph on the other axis. The time phase data acquisition apparatus 50 acquires and transmits the time phase data Pi corresponding to the acquisition request. The time phase data acquiring unit 113 receives this pulse wave data Pi from the time phase data acquisition apparatus 50 via the LAN 30. The time phase data acquiring unit 113 stores the received time phase data Pi in the storage unit 120. Now, there are two conceivable timings relating acquisition of the time phase data Pi by the time phase data acquisition apparatus 50; one is a case where the confocal data acquiring unit 111 or non-confocal data acquiring unit 112 starts image acquisition in conjunction with a particular phase of the time phase data Pi, the other is a case where acquisition of time phase data Pi and image acquisition are simultaneously started immediately after an image acquisition request. In the present embodiment, acquisition of pulse wave data Pi and image acquisition are simultaneously started immediately after an image acquisition request. The time phase data Pi of each image is acquired by the time phase data acquiring unit 113, the extreme value in each time phase data Pi is detected, and the cardiac cycle and relative cardiac cycle are calculated. FIGS. 6C and 6D illustrate an example of a confocal image Dc and non-confocal image Dnr in a case of having photographed a retinal blood vessel. The confocal image Dc has strong reflection from the nerve fiber layer in the background, so the background noise makes positioning difficult. The non-confocal image Dnr (Dnl) of the R channel (L channel) has higher contrast at the blood vessel wall at the right side (left side).

Figure 6E:
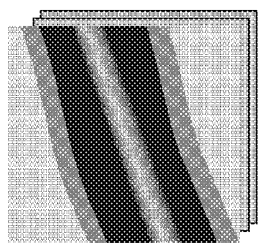
Figure 6F:
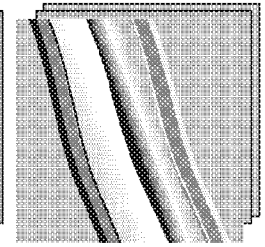

On the other hand, examples of non-confocal images are not limited to this. Other examples include an addition process image Dnr+l of non-confocal images Dnr and Dnl, and a Split Detector images Dnsd to which a type of differential processing ((L−R)/(R+L)) has been applied. FIGS. 6E and 6F illustrate examples of Dnr+l and Dnsd. Background noise is reduced and the edges of blood vessels are enhanced in Dnr+l and Dns, so robust and accurate positioning can be performed in comparison with confocal images Dc. In the following, when non-confocal image Dnk is mentioned, any non-confocal images Dnk may be used, but if not stated in particular, Dnr+l will be used.

Step S520: Inter-Frame Positioning

The positioning unit 131 performs inter-frame positioning in the wide-angle images Dln and non-confocal images Dnk. A reference frame to serve as the reference for positioning is set for wide-angle images Dln and non-confocal images Dnk, and general positioning (rough positioning) is performed by Affine transformation. Further, non-rigid positioning is performed as precision positioning. Note that in this step, the exemption region determining unit 1310 detects exemption frames with luminance abnormality, image distortion, low sound-to-noise (S/N) ratio and frame-out, in the wide-angle images Dln and non-confocal images Dnk.

Alternatively, inter-frame positioning parameters decided with regard to the wide-angle images Dlnr+l and non-confocal images Dnr+l are applied to not only Dlnr+l and Dnr+l but also to wide-angle images Dlc, Dlr, and Dll, confocal images Dcj, and non-confocal images Dnr and Dnl, and inter-frame positioning is performed. Further, inter-frame positioned moving images (FIG. 6G) are subjected to processing where only frames having a particular phase in the time phase data Pi are selected, and thereupon the positioning parameter values decided in this step are used to composite the moving images Dl, Dcj, and Dnk (FIG. 6H). The particular phase specified here is the end-diastole. A specific inter-frame positioning method will be described in detail in S710 through S750.

Step S530: Tiling Images

The positioning unit 131 positions the composited image of wide-angle non-confocal images Dln and high-magnification non-confocal images Dnk formed in S520, and finds the relative position of Dnk on Dln. That is to say, the inter-image similarity is calculated for the wide-angle non-confocal image Dlnr+l and high-magnification non-confocal image Dnr+l while changing combinations of the positioning parameter values. The combination of positioning parameter values where the similarity is highest is used to decide the relative position of each non-confocal image Dnr+l as to the wide-angle non-confocal image Dlnr+l.

Further, the positioning parameters decided regarding the wide-angle non-confocal image Dlnr+l and high-magnification non-confocal image Dnr+l are also applied to tiling of the confocal images (Dlc and Dcj) and the non-confocal images of each channel (Dlr and Dnrk, Dll and Dnlk) The relative position of the high-magnification image Dcj on the wide-angle image Dlc, the relative position of the wide-angle image Dnrk on the wide-angle image Dlr, and the relative position of the high-magnification non-confocal image Dnlk on the wide-angle image Dll, are decided. A specific image tiling method will be described in detail in S711 through S721.

Step S540: Display

The display control unit 132 displays the formed image group on the monitor 305. Here, only frames having a particular phase in phase time data Pi (end-diastole) are selected, the moving images are composited using the positioning parameters decided in S520, and the images obtained thereby are displayed in a tiled manner using the positioning parameters decided in S530. A composited image or inter-frame positioned moving image is displayed for the imaging position instructed via the instruction acquiring unit 140, using the inter-frame positioning parameters decided in S520.

The type of images to be display are switched using a graphical user interface (GUI) that has been prepared for this purpose. Although radio buttons are used for switching in the present embodiment, any GUI arrangement may be used for the switching. The types of images to be switched are not restricted to the three types of confocal, R channel, and L channel, and may include image s generated by any computation among these images. For example, the five types of confocal images, R-channel images, L-channel images, R+L images, and Split Detector images ((L−R)/(R+L)) may be switched and displayed.

The display control unit 132 may perform display correcting the concentration among confocal images Dcj and among non-confocal images Dnk, in a case where multiple confocal images Dcj and non-confocal images Dnk have been acquired. Any known luminance correction method may be used. In the present embodiment, the concentration difference is corrected by performing linear transformation of luminance values of each image Dcj and Dnk so that the averages and variances of histograms Hj and Hk, generated at the images Dcj and Dnk, are common between the images Dcj and Dnk. Note that the method of luminance correction among confocal images and non-confocal images is not restricted to this, and any known luminance correction method may be used. Further, an image specified by the operator via the instruction acquiring unit 140 is enlarged to an instructed display scale and displayed on the monitor 305.

Step S550: Whether or not to Save Results

The instruction acquiring unit 140 externally acquires instructions regarding whether or not to save in the data server 40 the wide-angle images Dlc, Dlr, and Dll, high-magnification confocal images Dc, high-magnification non-confocal images Dnr and Dnl, fixation target positions Fl and Fcn, the positioning parameter values acquired in S520 and S530, and the composited images and tiled images formed in S540. This instruction is input by an operator by way of the keyboard 306 or mouse 307, for example. In a case where an instruction for saving has been given, the flow advances to S560, and if saving is not instructed, the flow advances to S570.

Step S560: Saving Results

The image processing unit 130 transmits to the data server 40 examination date, information identifying examinee eye, wide-angle images Dlc, Dlr, and Dli, high-magnification images Dc, Dnr, Dnl, fixation target positions Fl and Fcn, the positioning parameter values, and the composited images and tiled images of the moving images Dlc, Dlr, Dll, Dc, Dnr, and Dnl, in a correlated manner.

Step S570: Decision of Whether or not to End

The instruction acquiring unit 140 externally acquires an instruction regarding whether or not to end processing of the wide-angle images Dl, high-magnification confocal images Dcj, and high-magnification non-confocal images Dnk, by the information processing apparatus 10. This instruction is input by an operator by way of the keyboard 306 or mouse 307, for example. In a case where an instruction for ending of processing is acquired, the processing ends. On the other hand, in a case of acquiring an instruction to continue processing, the flow returns to S510, and processing on the next examinee eye (or redoing the processing on the same examinee eye) is performed.

Figure 7A:
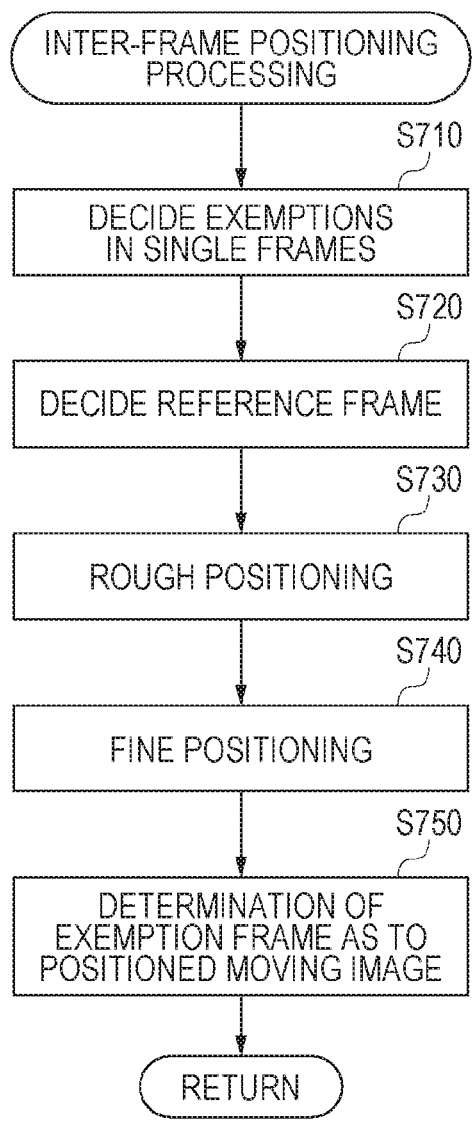
FIGS. 7A and 7B are flowcharts illustrating the details of processing executed in S520 and S530 according to the first embodiment and a fourth embodiment, and in S532 and S542 in a third embodiment.

The processing executed in S520 will be described in detail with reference to the flowchart in FIG. 7A.

Step 710: Determining Exemption Frames

Exemption frame determination is performed for each frame in the high-magnification non-confocal images Dnk, in increments of individual frames. The exemption region determining unit 1310 calculates the average luminance value Akj and S/N ratio SNj of each frame. Of the Akj is not above a threshold T1, or the S/N ratio SNj is not above a threshold T2, the frame is found either to have a luminance abnormality or to be low in image quality, and is determined to be an exemption frame. Note however, that the exemption frame determination method is not restricted to this, and any exemption determination method may be used.

Step S720: Deciding Reference Frame

The positioning unit 131 sets a reference frame to serve as a positioning for the high-magnification non-confocal images Dnk. In the present embodiment, the frame with the smallest frame number other than frames determined to be exemption frames in S710 is the reference frame. Note that the frame setting method is not restricted to this, and any setting method may be used. For example, a reference frame number that the user has specified may be acquired from the instruction acquiring unit 140 and the reference frame thus set.

Step S730: Rough Positioning

The positioning unit 131 performs general inter-frame correlation (rough positioning) for the high-magnification non-confocal images Dnk. Any positioning technique may be used, and the present embodiment performs rough positioning using a correlation coefficient as an inter-image similarity evaluation function, and Affine transform as a coordinate conversion technique. The evaluation function and coordinate conversion technique are not restricted to these, and any evaluation function or coordinate conversion technique may be used.

Step S740: Fine Positioning

The positioning unit 131 performs fine positioning of the high-magnification non-confocal images Dnk based on the correspondence relation in the general position among the frames of the high-magnification non-confocal images Dnk obtained in S730. In the present embodiment, the moving image obtained by the high-magnification non-confocal images Dnk being subjected to the rough positioning in S730 are then subjected to inter-frame fine positioning, using free form deformation (FFD), which is a type of a non-rigid positioning technique. Note that the fine positioning technique is not restricted to this, and any positioning technique may be used.

Step S750: Determining Exemption Frame as to Positioned Moving Image

Exemption frame determination is performed as to the frames of the fine-positioned moving image obtained by the fine positioning of high-magnification non-confocal image Dnk in S740. In the present embodiment, the exemption region determining unit 1310 performs differential calculation of each frame that is not the reference frame, as to the reference frame, and obtains a histogram of differential images. If the average value and variance of the histogram are a threshold T3 or higher and a threshold T4 or higher, respectively, determination is made that a different position on the fundus has been imaged temporarily due to involuntary eye movement, and the frame is determined to be an exemption frame.

The exemption frame determination method is not restricted to this, and any determination method may be used. For example, blood vessel extraction and blood vessel intersection detection is performed on each frame in the fine-positioned moving image of high-magnification non-confocal image Dnk. An arrangement may be made where the sum of squares of the distance between blood vessel intersections is calculated in each frame, and if the value of the sum of squares is different from that in an adjacent frame by a threshold T5 of more, determination is made that distortion has occurred, and the frame is determined to be an exemption frame.

Figure 7B:
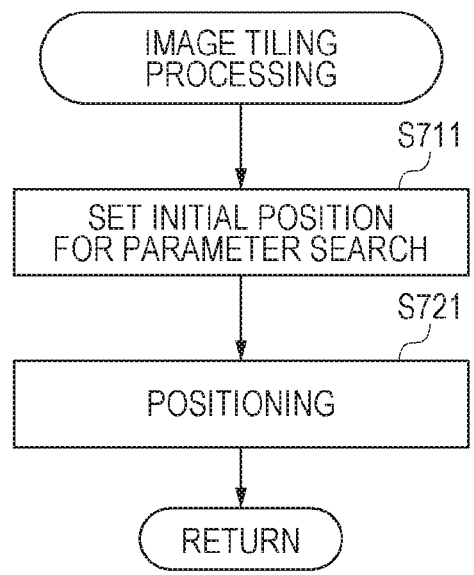

Next, the processing performed in S530 will be described in detail with reference to the flowchart in FIG. 7B.

Step S711: Setting Initial Position for Parameter Search

The positioning unit 131 acquires the fixation target position Fcn used at the time of imaging the high-magnification non-confocal images Dcj from the storage unit 120, to use as the initial point for searching for positioning parameters for the positioning of the wide-angle image Dln and non-confocal image Dnk. The positioning parameters obtained in the present embodiment are translation (x and y), rotation θ, and enlargement factor s. The initial values set for the parameters are (x0, y0, θ0, s0)=(x component of Fcn, y component of Fcn, 0°, 1.0).

Step S721: Positioning

The combination of parameter values (x0, y0, θ0, s0) set in S711 are used as initial values, and positioning of the wide-angle image Dln and high-magnification non-confocal image Dnk is performed while changing the combination of parameter. In the present embodiment, the wide-angle image Dln is a composited image. A combination of positioning parameters where the similarity between the composited image of wide-angle image Dln and the composited image of high-magnification non-confocal image Dnk is the highest, is decided to be the relative position of the wide-angle image Dln as to the high-magnification non-confocal image Dnk. The positioning technique is not restricted to this, and any positioning technique may be used. In a case where there is an overlapping region among high-magnification non-confocal images Dnk, the inter-image similarity is calculated for this overlapping region as well, and the high-magnification non-confocal images Dnk are positioned as to each other where the inter-image similarity is the highest.

In a case where a mid-magnification image has been acquired in S510, positioning is performed from images with lower magnification. For example, in a case where a high-magnification non-confocal image Dc1m and a mid-magnification non-confocal image Dc2o have been acquired, first, the wide-angle image Dlc and the mid-magnification image Dc2o are positioned, and next, the mid-magnification image Dc2o and the high-magnification confocal image Dnlm are positioned.

Although the present embodiment uses pixel-value-based inter-image similarity to find a parameter combination where all frames of the high-magnification moving image Dnk have the highest similarity to the reference frame or the wide-angle image Dln, as the relative position on wide-angle image Dln, this is not restrictive. For example, image features of objects of observation (portions such as disorders or the fovea, feature points such as blood vessel branch points, and so forth) may be detected in the frames of the high-magnification moving image Dnk or the wide-angle image Dln. Positioning may be performed among frames of the high-magnification moving image Dnk or among the wide-angle image Dln and high-magnification moving image Dnk, so that the positions of features most precisely match.

Also, although description has been made in the present embodiment where the wide-angle image Dln is a moving image and positioning is performed between a composited image of the wide-angle image Dln and non-confocal images Dnk, this is not restrictive. For example, the wide-angle image Dln may be a sill image, with positioning being performed as to a predetermined frame (reference image) of Dln. Also, a case where a wide-angle image Dl only includes rect-confocal images is also included in the present invention. In this case, a similarity evaluation function value used in positioning of multi-modality images, such as mutual information content, may be calculated between a composited image of wide-angle image Dlc and a composited image of high-magnification image Dnr+l, and positioning performed at a positioning parameter value where the evaluation value is the largest.

The images to be tiled and displayed are not restricted to confocal images and non-confocal images. Images generated by performing image processing thereon may be tiled and displayed using the positioning parameters decided in S520 and S530. For example, an angiogram (a so-called perfusion image) can be generated by mutually dividing adjacent frames in an inter-frame-positioned moving image, and calculating a standard deviation of the division value at each pixel position in all frames (FIG. 6I). Performing tiling and displaying of the angiograms using the positioning parameters decided in S530 is also included in the present invention.

Further, an arrangement may be made where the high-magnification moving image Dcj (Dnk) instead of a still image is tiled upon the wide-angle image Dlc (Dln) and displayed synchronously. In a case of performing synchronous display, the longest continuous frame interval excluding exemption frames is found in each moving image, and the playback cycle of the moving images can be matched with each other by interpolation processing of the frames of the moving images. Of course, in a case where no time phase data has been acquired, the moving images may be tiled and displayed without adjusting the playback point-in-time or playback cycle.

According to the configuration described above, the information processing apparatus 10 performs the following processing when imaging retinal blood vessels using the SLO apparatus at acquires confocal images Dc and non-confocal images Dn at the same time. That is to say, the information processing apparatus 10 performs inter-frame positioning and image tiling processing of the confocal images Dc and non-confocal images Dn using positioning parameter values decided based on the non-confocal images Dn. Accordingly, images taken of blood vessels at the inner layer of the retina can be robustly and highly accurately positioned.

Second Embodiment: Tracking Processing Using Non-Confocal Images

The information processing apparatus 10 according to a second embodiment is configured such that, at the time of imaging retinal blood vessels using an SLO apparatus that acquires confocal images and non-confocal images at the same time, performs tracking processing using non-confocal images while acquiring images, instead of performing positioning after acquiring images as in the first embodiment. The term "tracking processing" as used here refers to performing high-speed image positioning at each local region, giving feedback of the results thereof to the SLO apparatus, and correcting the scanning position of the scanner as necessary. Specifically, an SLO apparatus such as illustrated in FIGS. 3A and 3B that acquires confocal images Dcj and non-confocal images Dnk at generally the same time, acquires non-confocal images Dnk of retinal blood vessels. A case will be described regarding performing tracking using translation movement parameters decided based on similarity evaluation values among adjacent rectangular regions, the screen having been divided into multiple rectangular regions.

The configuration of apparatuses connected to the information processing apparatus 10 according to the present embodiment is the same as in the first embodiment. In addition to the wide-angle images Dlc, Dlr, and Dli, and high-magnification images Dcj, Dnrk, and Dnlk, of the examinee eye, and acquisition conditions such as the fixation target positions Fl and Fcn used at the time of acquisition, the data server 40 also holds image features of the eye. Any image features of the eye may be used, but the present embodiment handles retinal blood vessels blood vessel walls, capillaries Q, and blood cells W. Image features of the eye, output from the information processing apparatus 10 are saved in the data server 40. The image features of the eye are transmitted to the information processing apparatus 10 upon request by the information processing apparatus 10.

Figure 5B:
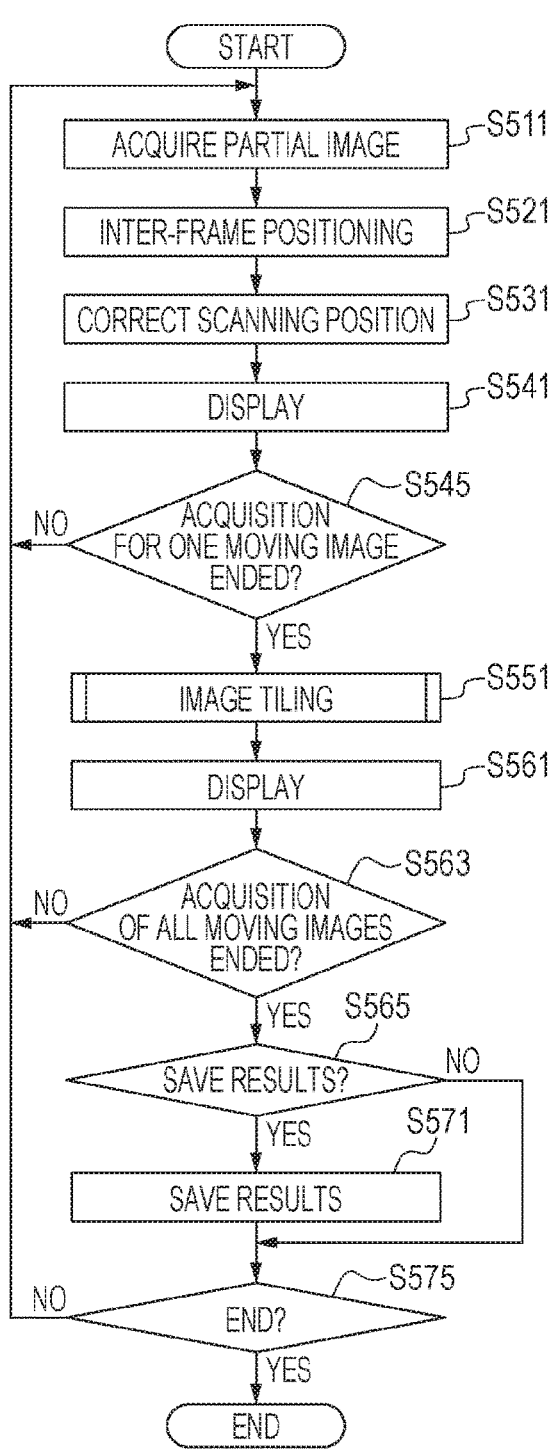
Figure 8:
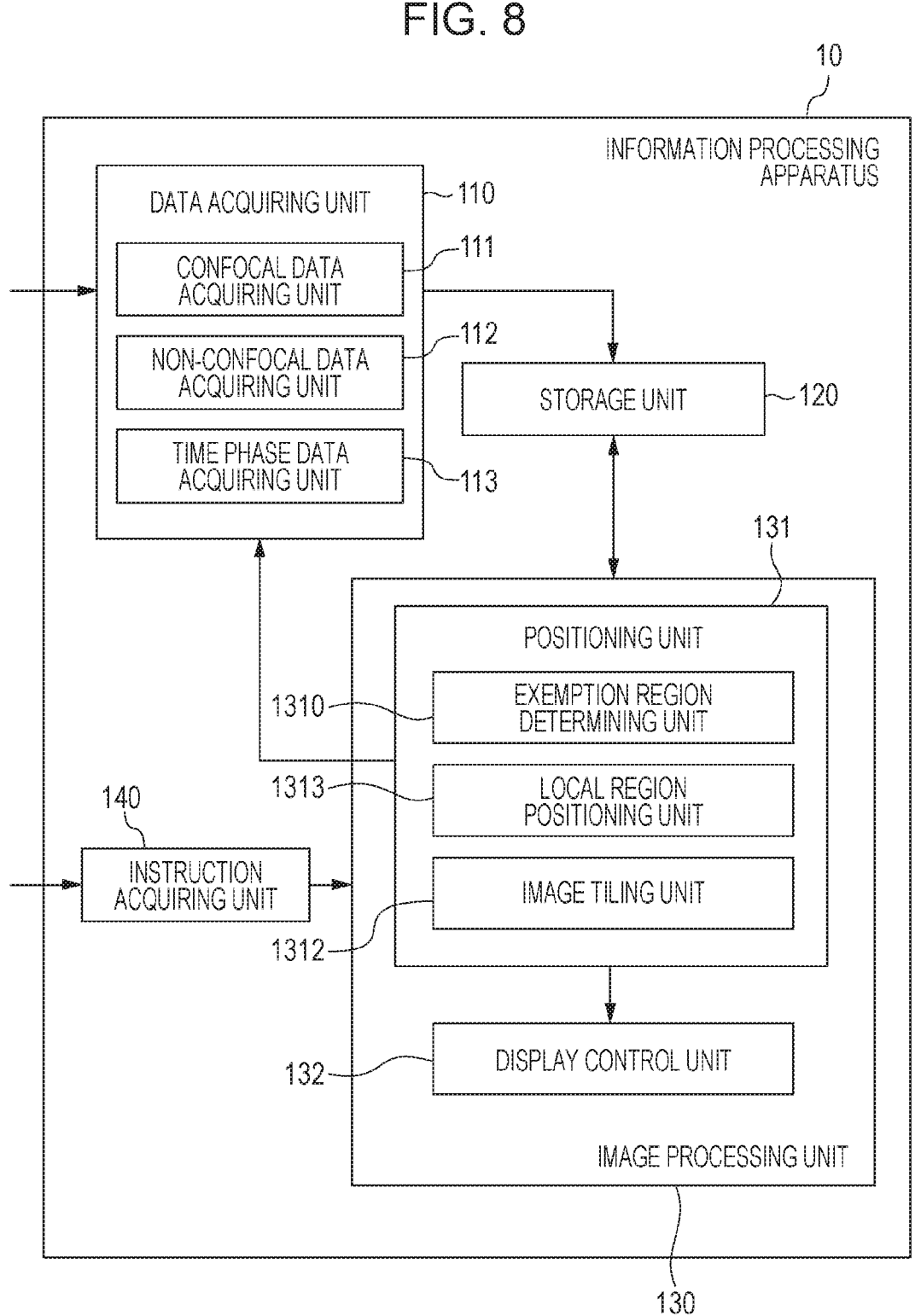
FIG. 8 is a block diagram illustrating a functional configuration example of an information processing apparatus according to a second embodiment.

Next, FIG. 8 illustrates a functional block diagram of the information processing apparatus 10 according to the present embodiment. This configuration differs from the first embodiment with regard to the point that the positioning unit 131 has a local region positioning unit 1313. This arrangement also differs from the first embodiment in that inter-local-region positioning parameter values are transmitted to the data acquiring unit 110, the data acquiring unit 110 performs feedback thereof to the SLO imaging apparatus 20, and the scanning position of the X-Y scanning mirror 205 is corrected. The image processing flow according to the present embodiment is the same as that illustrated in FIG. 5B, where S561, S565, S571, and S575 are the same as in the first embodiment. Accordingly, the processing of S511, S521, S531, S541, S545, S551, and S563, will be described in the present embodiment. Note that in the present embodiment, the frame numbers of the high-magnification image Dnk are denoted by p (p=1, 2, . . . , pmax), with the p'th frame of a non-confocal high-magnification image Dnk being written as Dnkp.

Step S511: Acquisition of Partial Image

Figure 6G:
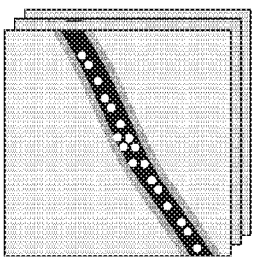
Figure 6H:
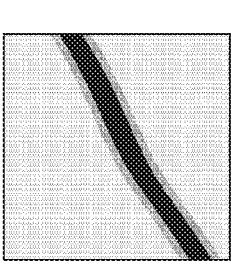
Figure 6I:
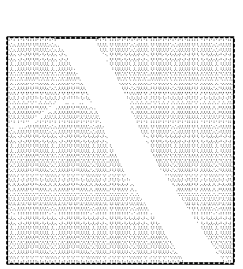
Figure 6J:
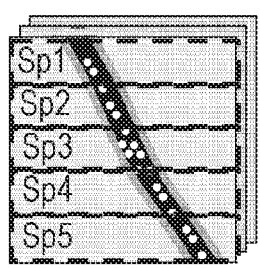

The data acquiring unit 110 acquires, as a partial image within the p'th frame Dnkp of non-confocal high-magnification moving image Dnk, Spx (x=1, 2, . . . , xmax) The main scanning direction of the high-magnification moving image Dnk is the lateral direction, so the partial regions Spx of the non-confocal high-magnification moving image Dnk such as illustrated in FIG. 6G are defined as horizontally-long rectangular regions indicated by Sp1 through Sp5 in FIG. 6J. Any natural number values may be used for the vertical and horizontal size of the local regions (partial regions), as long as 1 or larger and within the image size. Any shape may be specified for the local regions. In a case of acquiring the next partial image after the last partial image (Sp5 in FIG. 6J) has been placed at the bottom of the frame in the present embodiment, the partial image S(p+1)1 at the top of the next frame is acquired.

Step S521: Positioning within Frame

Upon the partial image Spx+1 of the non-confocal high-magnification moving image Dnkp being acquired by the data acquiring unit 110, The local region positioning unit 1313 performs positioning between the partial image Spx+1 and the adjacent partial image Spx. Specifically, similarity (or dissimilarity) evaluation values are calculated with regard to horizontal-direction and vertical-direction translation movement within a predetermined parameter search range. Any evaluation function may be used for evaluation values. In the present embodiment, cross-correlation coefficient values are used. Calculation of similarity evaluation values is repeated while changing the combination of parameter values, and a combination of translation movement amounts where the similarity evaluation value is the largest (the smallest in the case of a dissimilarity evaluation value). After the partial image at the bottom of the frame (Sp5 in FIG. 6J) is positioned, and the next partial image S(p+1)1 (the partial image at the top of the next frame) is acquired in S520, this is positioned with the partial image Sp1 at the top of the previous frame, and a positioning parameter value where the evaluation value is the largest is calculated.

Even in a case where the focus position is set on the inner layer of the retina to image blood vessels, positioning is performed within the frames of the non-confocal moving image, so the influence of background high-luminance noise can be eliminated, so more robust and highly accurate in-frame positioning can be performed as compared to a case of performing in-frame positioning with confocal images Dcj.

Step S531: Correcting Scanning Position

The positioning unit 131 transmits the positioning parameters to the data acquiring unit 110 based on the positioning parameter values decided by the local region positioning unit 1313 (horizontal and vertical translation movement amount between adjacent partial images). Further, the data acquiring unit 110 transmits the positioning parameters of the SLO imaging apparatus 20. The SLO imaging apparatus 20 corrects the scanning position of the X-Y scanning mirror 205 such that the calculated translation movement amount is canceled out.

Step S541: Display

The display control unit 132 connects the partial images based on the positioning parameter values calculated in S521 (translation movement amount in horizontal direction and vertical direction), and connects the partial images so as to display on the monitor 305 as a synthesized frame. The scanning position of the partial image Spx is corrected at each acquisition, so the synthesized frame is displayed as an almost completely stationary frame, and images of retinal blood vessels that can be clearly observed can be obtained a high speed.

Step S545: Determining Whether or not to End Acquisition of One Moving Image

The data acquiring unit 110 determines whether acquisition of the specified number of frames for imaging has been completed with regard to the moving images Dc, Dnr, and Dnl currently being imaged, and if image acquisition for one moving image has been completed, the flow advances to S551. If there are frame yet to be acquired, the flow advances to S511 and the SLO imaging apparatus 20 is requested to acquire the next partial image (Spx+1 or S(p+1)1).

Step S551: Tiling Images

The image tiling unit 1312 performs tiling of the non-confocal high-magnification images Dnk on the wide-angle images Dln. The basic tiling method is the same as in in the first embodiment. Note however, that while the first embodiment involved tiling all high-magnification images Dncj, Dnrk, and Dnlk on the wide-angle image at once, the present embodiment differs in that tiling onto the wide-angle images Dlc, Dnr, and Dnl is performed each time one high-magnification image Dncj, Dnrk, or Dnlk is acquired.

Step S563: Determination Whether or not to End Acquisition of all Moving Images

The data acquiring unit 110 determines whether or not acquisition of all moving images has ended, and if acquisition of all moving images has ended the flow advances to S565. If there remain moving images yet to be acquired, the flow advances to S511, and the SLO imaging apparatus 20 is requested to acquire the next moving image. Although the processing of this step is executed after S561 in the present embodiment, this may be performed after the processing of S571.

According to the configuration described above, at the time of imaging retinal blood vessels using the SLO apparatus that acquires confocal images Dc and non-confocal images Dn at the same time, the information processing apparatus 10 performs tracking processing using the positioning parameter values decided based on the non-confocal images Dn. Accordingly, images taken of blood vessels at the inner layer of the retina can be robustly and highly accurately positioned.

Third Embodiment: Deciding Type of Images to be Positioned

The information processing apparatus according to a third embodiment ides not perform positioning using positioning parameters decided from non-confocal images at all times as with the first embodiment, but rather decides the type of images to be positioned based on in-pane or depth-direction acquisition position of images, and decides positioning parameter values from this image type. Specifically, confocal images are decided to be used for positioning with regard to images taken of the outer layer of the retina at the macular area, and non-confocal images are decided to be used for positioning with regard to images taken of the inner layer of the retina at the optic disc. Inter-frame positioning and image tiling processing is performed using the decided type of images.

The configuration of apparatuses connected to the information processing apparatus 10 according to the present embodiment is the same as in the first embodiment. In addition to the wide-angle images Dlc, Dlr, and Dll, and high-magnification images Dcj, Dnr, and Dnl, of the examinee eye, and acquisition conditions such as the fixation target positions Fl and Fcn used at the time of acquisition, the data server 40 also holds image features of the eye. Any image features of the eye may be used, but the present embodiment handles retinal blood vessels blood vessel walls, capillaries Q, and blood cells W. Image features of the eye, output from the information processing apparatus 10 are saved in the data server 40. The image features of the eye are transmitted to the information processing apparatus 10 upon request by the information processing apparatus 10.

Figure 5C:
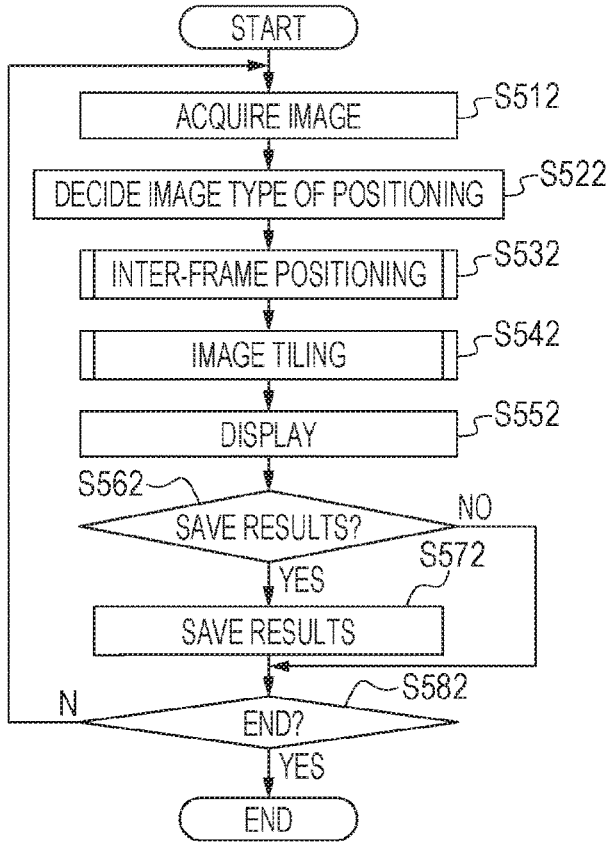
Figure 9:
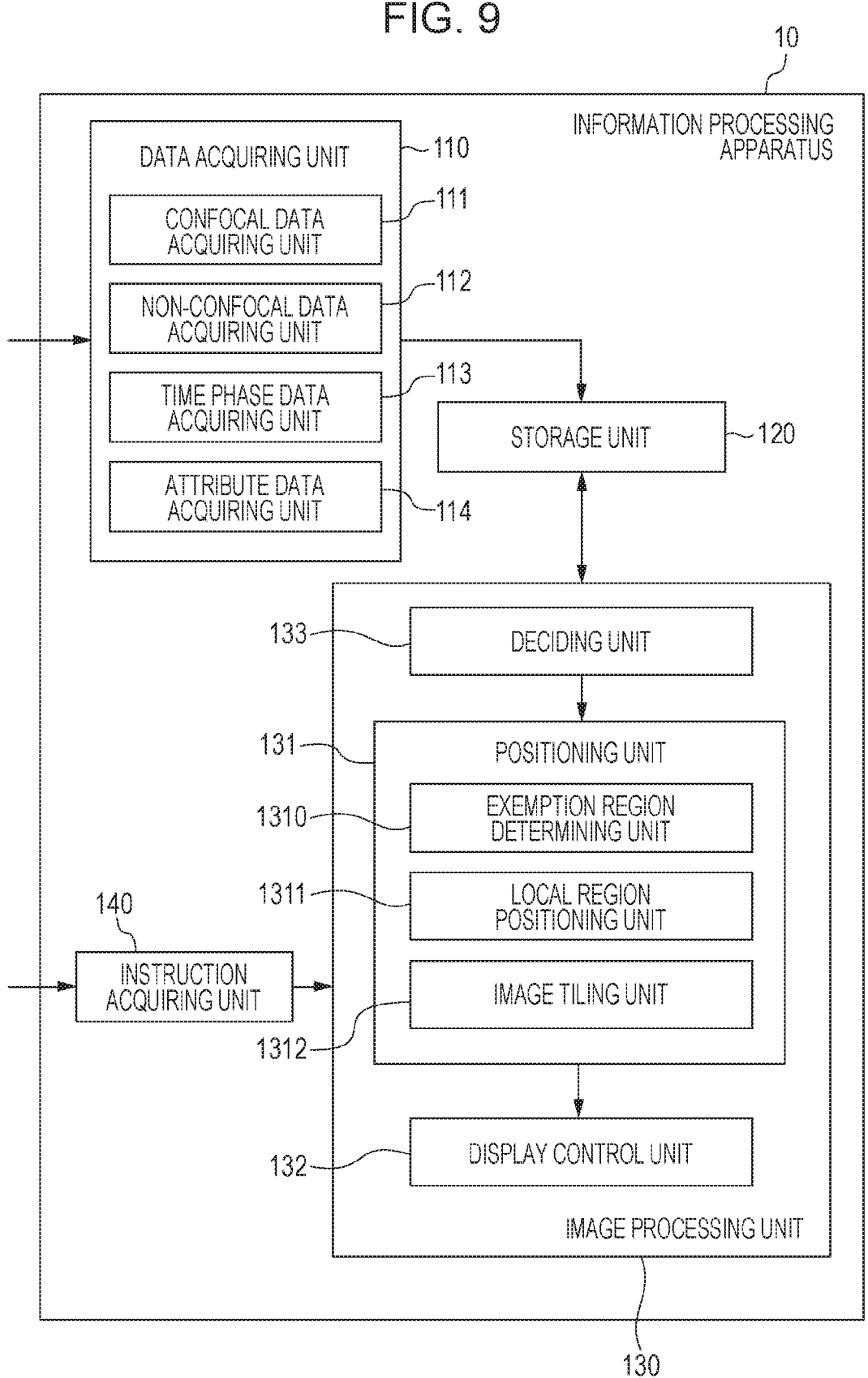
FIG. 9 is a block diagram illustrating a functional configuration example of an information processing apparatus according to a third embodiment.

Next, FIG. 9 illustrates a functional block diagram of the information processing apparatus 10 according to the present embodiment. This configuration differs from the first embodiment with regard to the point that the data acquiring unit 110 has an attribute data acquiring unit 114, and the image processing unit 130 has a deciding unit 133. The image processing flow according to the present embodiment is the same as that illustrated in FIG. 5C, where other than S512, S522, S532, S542, and S552 are the same as in the first embodiment. Accordingly, just the processing of S512, S522, S532, S542, and S552, will be described in the present embodiment.

Step S512: Acquiring Images

The confocal data acquiring unit 111 acquires wide-angle images Dlc, and the confocal high-magnification images Dlc at the outer layer of the retina at the macular area, and at the inner layer of the retina at the optic disc. The non-confocal data acquiring unit 112 acquires wide-angle images Dlr and Dll, and non-confocal images Dnr and Dnl at the outer layer of the retina at the macular area, and at the inner layer of the retina at the optic disc. The attribute data acquiring unit 114 acquires the acquisition position (in-plane and depth direction) as the attributes of the images which the confocal data acquiring unit 111 and the non-confocal data acquiring unit 112 have acquired. The object of observation at this time is photoreceptors at the outer layer of the retina at the macular area, and retinal blood vessels at the inner layer of the retina at the optic disc. Time phase data Pi is also acquired at the same time at the inner layer of the retina at the optic disc.

Step S522: Deciding Type of Image for Positioning

In S512, the deciding unit 133 decides the image type to use for frame positioning and tiling of the images, based on the image acquisition position data acquired by the attribute data acquiring unit 114. In the present embodiment, the deciding unit 133 decides non-confocal images to be used for positioning at the optic disc or inner layer of the retina, and otherwise to use confocal images.

Step S532: Inter-Frame Positioning

The inter-frame positioning unit 1311 performs inter-frame positioning processing on the images acquired in S512, using the type of image decided in S522. The procedures for inter-frame positioning basically are the same as S710 through S750 in the first embodiment. However, one point differs from the first embodiment in that inter-frame positioning is performed using the type of images decided by the deciding unit 133, and the positioning parameter values obtained as a result thereof are used to perform inter-frame positioning of other types of images. That is to say, at the inner layer of the retina at the optic disc, a non-confocal moving image Dnr+l is generated, and thereafter inter-frame positioning processing of the moving image is performed, and the inter-frame positioning parameter values obtained thereby are used for inter-frame positioning of a confocal moving image Dc. Also, at the outer layer of the retina at the macular area, inter-frame positioning of a confocal moving image Dc performed, and the inter-frame positioning parameter values obtained thereby are used for inter-frame positioning of a non-confocal moving image Dnk. Further, the inter-frame-positioned moving images that are obtained are subjected to compositing processing, thereby generating a composited image. When generating a composited image including images of the inner layer of the retina at the optic disc regarding which time phase data Pi has been acquired, frames belonging to an interval having a predetermined pulse wave phase are selected, to prevent the composted image from becoming blurred due to change in blood vessel diameter from the heartbeat.

Step 542: Tiling Images

The image tiling unit 1312 performs tiling processing of the images generated in S532. The procedures for tiling processing basically are the same as S711 through S721 in the first embodiment. However, one point differs from the first embodiment in that tiling processing is performed using the type of images decided by the deciding unit 133, and the positioning parameter values obtained as a result thereof are used to perform tiling processing of other types of images.

That is to say, at the inner layer of the retina at the optic disc, an image is generated by compositing generated non-confocal images Dnr+l, and thereafter tiling processing of the images is performed, and the parameter values obtained thereby are used for tiling processing of the confocal image Dc. Also, at the outer layer of the retina at the macular area, an image is generated by compositing generated confocal images Dc, and the parameter values obtained thereby are used for tiling processing of the non-confocal image Dnr+l.

Step 552: Display

The display control unit 132 displays the formed image group on the monitor 305. In the present embodiment, an image tiled based on the positioning parameters decided in S542 is displayed. A composited image or inter-frame-positioned moving image at a imaging position instructed via the instruction acquiring unit 140 is displayed using the inter-frame positioning parameter values decided in S532. The type of image to be displayed may be changed depending on the imaging position. In the present embodiment, the non-confocal (R+L) image Dnr+l is selected as a preset display setting for display of the optic disc, and the confocal image Dc for the macular area. The display control unit 132 may have a GUI for batch switching of image types to be displayed by the imaging position. For example, image types of imaging positions within ranges specified by rectangular or elliptical regions may be batch switched, or ranges in depth position may be specified in batch fashion by a slider indicating the depth position. Further, imaging position and depth position ranges may be specified in batch fashion by input of numerical values, to batch switch the image type to be displayed at multiple imaging positions.

According to the above-described configuration, the information processing apparatus 10 can decide an image type to use for positioning, based on the acquisition position of images in the in-plane direction or depth direction, and use the decoded type of image to decide inter-image positioning parameter values. Accordingly, images imaged of blood vessels at the inner layer of the retina, and photoreceptors at the outer layer of the retina, can be robustly and highly accurately positioned.

Figure 6K:
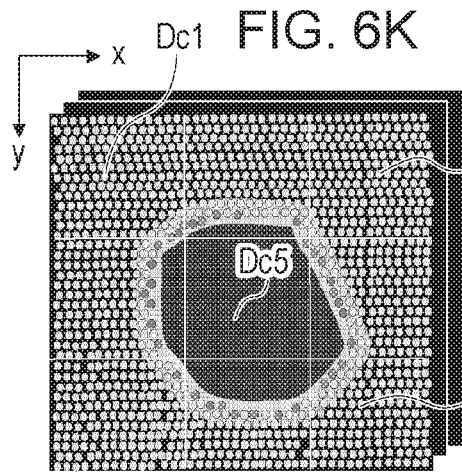
Figure 6L:
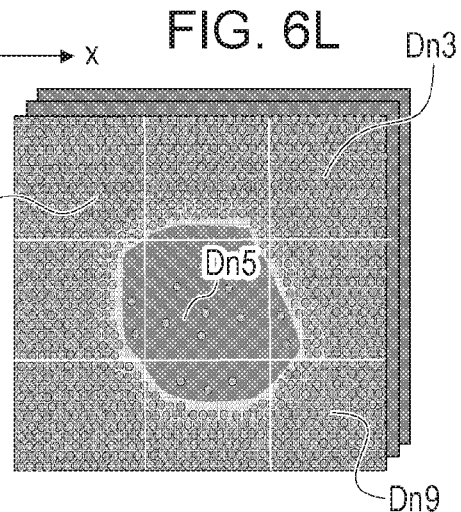

Fourth Embodiment: Evaluating Inter-Image Similarity for Each Image Type, and Decide Type of Image to Use for Positioning Based on Evaluation Results The information processing apparatus according to a fourth embodiment is configured to calculate inter-frame similarity evaluation values and similarity evaluation values for tiling, for all types of images, and use the type of image with the highest similarity evaluation value for inter-frame positioning and tiling. Specifically, the similarity between confocal images and the similarity between non-confocal images are calculated when acquiring confocal images and non-confocal images including a photoreceptor defect region at different imaging positions, as illustrated in FIGS. 6K and 6L, and selecting the image with higher similarity to perform positioning. Description will be made regarding a case of performing positioning based on confocal images in a region where the outer segments of the photoreceptors are sound, and non-confocal images in a region where the outer segments of the photoreceptors are defective. The configuration of the apparatuses connected to the information processing apparatus 10 according to the present embodiment differs from the first embodiment in that the time phase data acquisition apparatus 50 is not connected.

Figure 10:
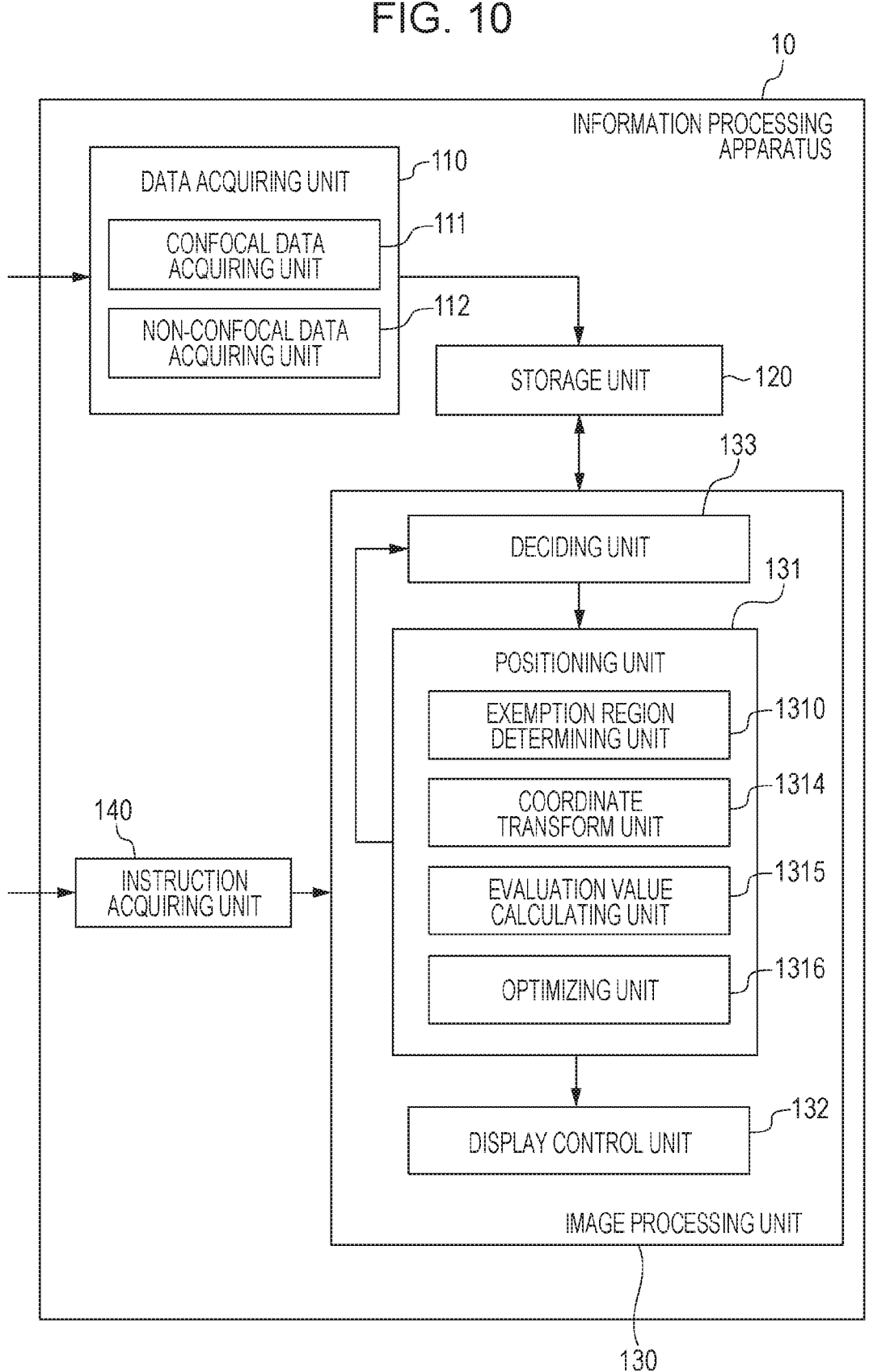
FIG. 10 is a block diagram illustrating a functional configuration example of an information processing apparatus according to a fourth embodiment.

Next, FIG. 10 illustrates a functional block diagram of the information processing apparatus 10 according to the present embodiment. This configuration differs from the first embodiment with regard to the point that the data acquiring unit 110 does not have the time phase acquiring unit 113, and that the positioning unit 131 is provided with a coordinate transform unit 1314, an evaluation value calculating unit 1315, and an optimizing unit 1316. The image processing flow according to the present embodiment is that illustrated in FIG. 5A, where other than S510, S520, S530, and S540, are the same as in the first embodiment. Accordingly, just the processing of S510, S520, S530, and S540, will be described in the present embodiment.

Step S510: Acquiring Images

The information processing apparatus 10 acquires information relating to user-specified image acquisition patterns (imaging position, etc.), via the instruction acquiring unit 140. In the present embodiment, fixation target positions Fl and Fcn are set at the fovea of the macular area and the high-magnification confocal images Dcj (j=1, 2m ..., 9) illustrated in FIG. 6K and the high-magnification non-confocal images Dnrk and Dnlk (k=1, 2, ..., 9) illustrated in FIG. 6L are acquired. Note that the setting method of imaging position is not restricted to this, and may be set to any position. The data acquiring unit 110 requests the SLO imaging apparatus 20 for wide-angle images Dlc, Dlr, and Dll, confocal images Dcj, non-confocal images Dnrk and Dnlk, and corresponding fixation target positions Fl and Fcn. In the present embodiment, images are acquired with the fixation target positions Fl and Fcn set to the fovea of the macular area. The SLO imaging apparatus 20 acquires and transmits the wide-angle images Dlc, Dlr, and Dll, confocal images Dcj, non-confocal images Dnrk and Dnlk, and corresponding fixation target positions Fl and Fcn in response to this acquisition request. The data acquiring unit 110 receives the wide-angle images Dlc, Dlr, and Dll, confocal images Dcj, non-confocal images Dnrk and Dnlk, and corresponding fixation target positions Fl and Fcn from the SLO imaging apparatus 20 via the LAN 30, and stores in the storage unit 120. The non-confocal data acquiring unit 112 in the present embodiment generates Split Detector images Dlnsd and Dnsdk as non-confocal images, and stores these in the storage unit 120. Hereinafter, wherever non-confocal images Dln and Dnk are mentioned, in reality positioning is being performed using the Split Detector images Dlnsd and Dnsdk.

Step S520: Inter-Frame Positioning

The positioning unit 131 performs inter-frame positioning at each imaging position. In the present embodiment, the similarity evaluation value of the high-magnification confocal image Dcj as to the confocal wide-angle image Dlc is compared with the similarity evaluation value of the high-magnification non-confocal image Dln as to the non-confocal wide-angle image Dnk, and inter-frame position is performed using the image type with the higher evaluation value. The specific processes for inter-frame positioning of each of the image types is the same as S710 through S750 in the first embodiment, differing only with regard to the point that there are cases where the images used for inter-frame positioning are confocal images instead of non-confocal images. For example, in the confocal image Dc5 in FIG. 6K, the photoreceptors are defective and highly accurate positioning is difficult since the similarity evaluation value is low, but in the non-confocal image Dn5 in FIG. 6L, the inner segments of the photoreceptors remain, so the evaluation value is high and inter-frame positioning can be performed with higher accuracy. Accordingly, the deciding unit 133 decides that at the fifth imaging position, the non-confocal image Dn5 is to be used as an image for positioning, and inter-frame positioning of the confocal image Dc5 is performed using the inter-frame positioning parameter value decided using the non-confocal image Dn5. At other imaging positions, for example at Dc1, the signal value of the confocal image is larger and the similarity evaluation value is higher than at the non-confocal image, so the deciding unit 133 decides the confocal images Dc1 as the inter-frame positioning image. Further, the positioning unit 131 performs inter-frame positioning of the non-confocal image Dn1 using the positioning parameter values decided using the confocal image Dc1.

Step S530: Tiling Images

The positioning unit 131 performs tiling at each imaging position. In the present embodiment, the similarity evaluation value of the high-magnification confocal image Dcj as to the confocal wide-angle image Dlc is compared with the similarity evaluation value of the high-magnification non-confocal image Dnk as to the non-confocal wide-angle image Dln, and tiling to the wide-angle image is performed using the image type with the higher evaluation value. The specific processes for inter-frame positioning of each of the image types is basically the same as the image tiling in the second embodiment, and tiling processing is not performed for all high-magnification images, but rather tiling processing of a single high-magnification image and wide-angle image is performed at each imaging position. The present embodiment differs from the second embodiment only with regard to the point that there are cases where tiling is performed based on confocal images as the result of the similarity evaluation comparison. For example, in the confocal image Dc5 in FIG. 6K, the photoreceptors are defective and the similarity evaluation value is low, so highly accurate tiling to wide-angle image is difficult, but in the non-confocal image Dn5 in FIG. 6L, the inner segments of the photoreceptors remain and the similarity evaluation value is high, so tiling can be performed with higher accuracy. Accordingly, the deciding unit 133 decides that at the fifth imaging position, the non-confocal image Dn5 is to be used as an image for tiling, and tiling of the confocal image Dc5 is performed using the tiling parameter value decided using the non-confocal image Dn5. At other imaging positions, for example at Dc1, the signal value is larger and the similarity evaluation value is higher than at the non-confocal image, so the deciding unit 133 decides the confocal images Dc1 as the tiling image. Further, the positioning unit 131 performs tiling of the non-confocal image Dn1 as to the wide-angle image Dnl using the tiling parameter values decided using the confocal image Dc1.

Step S540: Display

The display control unit 132 performs tiling of the image group formed so far based on the positioning parameters decided in S520 and S530, and displays on the monitor 305. Thus, inter-frame positioning and image tiling can be robustly performed regardless of whether a photoreceptor defect region or not. Description has been made in the present embodiment where images are taken at nine different shooing positions, inter-frame similarity evaluation values are calculated for all of the imaging positions, and inter-frame positioning is performed. Also, similarity evaluation values are calculated for all image types as to the wide-angle image at each imaging position, the image type with the highest evaluation value is decided at each imaging position and image tiling is performed, but the present invention is not restricted to this configuration. For example, an arrangement where the image is divided into multiple local regions, and similarity evaluation values calculated for all image types regarding inter-frame positioning and positioning as to the wide-angle image at each imaging position in each local region, and inter-frame positioning and image tiling is performed at each local region using the positioning parameter value decided using the image type of the highest evaluation value, is also included in the present invention.

According to the configuration described above, the information processing apparatus 10 calculates inter-frame similarity evaluation values for image so of all types, and similarity evaluation values among different imaging positions, and performs inter-frame positioning and image tiling processing using the image type with the highest evaluation value. Accordingly, images taken of a disorder at the outer layer of the retina can be robustly and highly accurately positioned.

Note that in the above-described embodiments, a configuration may be made where an image type for obtaining a positional gap is selectable from the above-described multiple types of images including non-confocal images. Accordingly, the user can find a positional gap using an optimal image type for the imaging position. Thus, acquisition of positional device can be improved.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-093541, filed Apr. 30, 2015, which is hereby incorporated by reference herein in its entirety.

What is claimed is:

1. An information processing apparatus comprising:
    an image acquiring unit configured to acquire types of images including a plurality of confocal images obtained by imaging an eye at different times, and a plurality of non-confocal images temporally corresponding to the plurality of confocal images, the plurality of confocal images and the plurality of non-confocal images being obtained with an optical member that splits returning light from the eye irradiated by light from a common light source, wherein the optical member splits the returning light into returning light passing through a confocal region and returning light passing through a non-confocal region; and
    an information acquiring unit configured to acquire, as information indicating a positional gap of at least one of the types of images, information indicating a positional gap of the plurality of non-confocal images in a case where the plurality of non-confocal images are selected.

2. The information processing apparatus according to claim 1, further comprising:
    a positioning unit that positions at least one of the types of images, based on the acquired information indicating the positional gap.

3. The information processing apparatus according to claim 2, further comprising:
    a deciding unit configured to decide, of the types of images, a type of image to be subjected to the positioning.

4. The information processing apparatus according to claim 3,
    wherein the deciding unit decides a type of image to be used for the positioning, based on at least one of
    an acquisition position where an image is acquired, and
    an inter-image evaluation value calculated for each acquired image.

5. The information processing apparatus according to claim 2,
    wherein the positioning unit performs at least one of
    inter-frame positioning,
    intra-local-region positioning within an image,
    image tiling, and
    positioning between the types of images.

6. The information processing apparatus according to claim 2, further comprising:
    a display control unit configured to display on a display unit an image positioned by the positioning unit.

7. The information processing apparatus according to claim 1,
    wherein an acquisition position of the plurality of confocal images and an acquisition position of the plurality of non-confocal images of the eye are the same.

8. The information processing apparatus according to claim 1,
    wherein the information processing apparatus is communicably connected to an ophthalmologic imaging apparatus that takes the types of images of the eye, and wherein the image acquiring unit acquires multiple types of images obtained by imaging the eye at generally the same time.

9. The information processing apparatus according to claim 8, further comprising:
a control unit configured to control the ophthalmologic imaging apparatus to track the eye, based on the information indicating a positional gap.

10. The information processing apparatus according to claim 8,
wherein the ophthalmologic imaging apparatus includes the common light source to acquire the plurality of confocal images and the plurality of non-confocal images of the eye, and
the optical member that splits returning light from the eye irradiated by light form the light source,
and wherein the image acquiring unit acquires the plurality of confocal images based on the returning light passing through the confocal region, and acquires the plurality of non-confocal images based on the returning light passing through the non-confocal region.

11. The information processing apparatus according to claim 10,
wherein the image acquiring unit acquires the confocal image and non-confocal image of the eye, obtained by adjusting at least one of a position and a shape of an aperture disposed upstream of a light-receiving portion that receives light of at least one of returning light passing through the confocal region and returning light passing through the non-confocal region.

12. The information processing apparatus according to claim 1, further comprising:
a selecting unit configured to select one of the types of images,
wherein the information acquiring unit acquires, in a case where a non-confocal image is selected as one of the types of images, the information indicating a positional gap of the plurality of confocal images, based on a positional gap of the plurality of non- confocal images.

13. The information processing apparatus according to claim 12,
wherein an acquisition position of the plurality of confocal images and an acquisition position of the plurality of non-confocal images of the eye are the same.

14. The information processing apparatus according to claim 12,
wherein the information processing apparatus is communicably connected to an ophthalmologic imaging apparatus that takes the types of images of an eye,
and wherein the image acquiring unit acquires multiple types of images obtained by imaging the eye at generally the same time.

15. An operation method of an information processing apparatus, the method comprising:
acquiring types of images including a plurality of confocal images obtained by imaging an eye at different times, and a plurality of non-confocal images temporally corresponding to the plurality of confocal images, the plurality of confocal images and the plurality of non-confocal images being obtained with an optical member that splits returning light from the eye irradiated by light from a common light source, wherein the optical member splits the returning light into returning light passing through a confocal region and returning light passing through a non-confocal region; and
acquiring, as information indicating a positional gap of at least one of the types of images, information indicating a positional gap of the plurality of non-confocal images in a case where the plurality of non-confocal images are selected.

16. A non-transitory computer-readable storage medium storing a program to cause a computer to execute the operation method according to claim 15.

17. The operation method of an information processing apparatus according to claim 15, further comprising:
selecting one of the types of images,
wherein the information indicating a positional gap of the plurality of confocal images is acquired, in a case where a non-confocal image is selected as one of the types of images, based on a positional gap of the plurality of non-confocal images.

18. The information processing apparatus according to claim 1, wherein the plurality of confocal images and the plurality of non-confocal images are obtained with a common adaptive optics system.

19. The information processing apparatus according to claim 1, wherein the plurality of confocal images and the plurality of non-confocal images are obtained with a common focus lens.

20. The information processing apparatus according to claim 1, wherein the plurality of confocal images and the plurality of non-confocal images are obtained with a common scanning optical system.

21. The information processing apparatus according to claim 1, wheren the optical member splits the returning light into spatially separate optical paths leading to spatially separate photosensors or spatially separate sections of a photosensor.

22. The information processing apparatus according to claim 1,
wherein the optical member includes a reflecting portion and one ore more transmitting portions, and
wherein the returning light passing through a confocal region is light reflected by the reflecting portion and the returning light passing through a non-confocal region is light transmitted through the one or more transmitting portions.

23. An information processing apparatus comprising:
an image acquiring unit configured to acquire selected at least one type of images among types of images including a plurality of confocal images obtained by imaging an eye at different times, and a plurality of non-confocal images temporally corresponding to the plurality of confocal images, the plurality of confocal images and the plurality of non-confocal images being obtained with an optical member that splits returning light from the eye irradiated by light from a common light source, wherein the plurality of confocal images being obtained using first returning light passing through a confocal region and the plurality of non-confocal images being obtained using second returning light passing through a non-confocal region; and
an information acquiring unit configured to acquire, as information indicating a positional gap of at least one of the types of images, information indicating a positional gap of the plurality of non-confocal images in a case where a type of the plurality of non-confocal images is selected.

24. The information processing apparatus according to claim 23, further comprising:
a positioning unit that positions at least one of the types of images, based on the acquired information indicating the positional gap.

25. The information processing apparatus according to claim 23, wherein the optical member splits the returning light into the first returning light passing through the confocal region and the second returning light passing through the non-confocal region.

26. The information processing apparatus according to claim 23, wherein the plurality of confocal images and the plurality of non-confocal images are obtained with a common adaptive optics system including an aberration correction unit that corrects a wave aberration using measurement result by a wavefront sensor.

27. The information processing apparatus according to claim 23, wherein the plurality of confocal images and the plurality of non-confocal images are obtained with a common focus lens.

28. The information processing apparatus according to claim 23, wherein the plurality of confocal images and the plurality of non-confocal images are obtained with the optical member that splits the returning light from the eye irradiated by light from a common scanning optical system that scans the eye with the light from the common light source.

29. An operation method of an information processing apparatus, the method comprising:

acquiring selected at least one type of images among types of images including a plurality of confocal images obtained by imaging an eye at different times, and a plurality of non-confocal images temporally corresponding to the plurality of confocal images, the plurality of confocal images and the plurality of non-confocal images being obtained with an optical member that splits returning light from the eye irradiated by light from a common light source, wherein the plurality of confocal images being obtained using first returning light passing through a confocal region and the plurality of non-confocal images being obtained using second returning light passing through a non-confocal region; and acquiring, as information indicating a positional gap of at least one of the types of images, information indicating a positional gap of the plurality of non-confocal images in a case where a type of the plurality of non-confocal images is selected.

30. A non-transitory computer-readable storage medium storing a program to cause a computer to execute the operation method according to claim 29.

* * * * *